US011197650B2

United States Patent
Kuehn et al.

(10) Patent No.: US 11,197,650 B2
(45) Date of Patent: Dec. 14, 2021

(54) COOLING SYSTEM FOR A COMPUTED TOMOGRAPHY DEVICE AND METHOD FOR COOLING A COMPUTED TOMOGRAPHY DEVICE

(71) Applicant: Siemens Healthcare GmbH, Erlangen (DE)

(72) Inventors: Ulrich Kuehn, Baiersdorf (DE); Friedrich Distler, Fuerth (DE); Hans-Juergen Mueller, Bretzfeld (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 1 day.

(21) Appl. No.: 16/820,946

(22) Filed: Mar. 17, 2020

(65) Prior Publication Data
US 2020/0315057 A1    Oct. 1, 2020

(30) Foreign Application Priority Data
Mar. 29, 2019   (DE) .......................... 102019204501.4

(51) Int. Cl.
*A61B 6/00* (2006.01)
*A61B 6/03* (2006.01)

(52) U.S. Cl.
CPC ............ *A61B 6/4488* (2013.01); *A61B 6/035* (2013.01)

(58) Field of Classification Search
CPC .............................. A61B 6/4488; A61B 6/035
See application file for complete search history.

(56) References Cited

U.S. PATENT DOCUMENTS

| 5,448,608 | A | * | 9/1995 | Swain | ................... | A61B 6/035 378/15 |
| 5,956,383 | A | * | 9/1999 | Kendall | .................. | H05G 1/02 378/199 |
| 2004/0228450 | A1 | | 11/2004 | Mueller | | |
| 2004/0240625 | A1 | * | 12/2004 | Kendall | ............... | A61B 6/4488 378/199 |

(Continued)

FOREIGN PATENT DOCUMENTS

| DE | 10304661 A1 | 12/2004 |
| DE | 102005041538 A1 | 3/2007 |
| DE | 102014205393 A1 | 9/2015 |

OTHER PUBLICATIONS

German Office Action for Application No. 10 2019 204 501.4 dated Nov. 12, 2019.

*Primary Examiner* — Chih-Cheng Kao
(74) *Attorney, Agent, or Firm* — Harness, Dickey & Pierce, P.L.C.

(57) ABSTRACT

A cooling system for a computed tomography device includes a fan for generating an air stream and a fan housing; first flow duct for guiding the air stream is formed in the fan housing and relatively widens out in a direction of flow of the air stream; and an annular frame for accommodating a rotational bearing. A rotating frame of the computed tomography device is connectable to the annular frame and is mounted rotatably relative to the annular frame about an axis of rotation. An annular second flow duct for guiding the air stream is formed in the annular frame and the fan is attached to the annular frame via the fan housing such that the fan is arranged outside the annular frame and the air stream is guided via the first flow duct from the fan to the annular second flow duct.

23 Claims, 6 Drawing Sheets

(56) References Cited

U.S. PATENT DOCUMENTS

| | | | |
|---|---|---|---|
| 2007/0053500 A1* | 3/2007 | Distler | A61B 6/035 378/199 |
| 2007/0053501 A1* | 3/2007 | Distler | A61B 6/4488 378/199 |
| 2007/0274437 A1* | 11/2007 | Schindler | A61B 6/035 378/20 |
| 2015/0270092 A1* | 9/2015 | Gruchatka | A61B 6/035 378/4 |
| 2015/0272525 A1* | 10/2015 | Kuhn | A61B 6/44 378/200 |
| 2016/0235377 A1* | 8/2016 | Yun | H05G 1/025 |
| 2019/0105005 A1* | 4/2019 | Arber | A61B 6/035 |

* cited by examiner

COOLING SYSTEM FOR A COMPUTED TOMOGRAPHY DEVICE AND METHOD FOR COOLING A COMPUTED TOMOGRAPHY DEVICE

PRIORITY STATEMENT

The present application hereby claims priority under 35 U.S.C. § 119 to German patent application number DE 102019204501.4 filed Mar. 29, 2019, the entire contents of which are hereby incorporated herein by reference.

FIELD

Embodiments of the invention generally relates to a cooling system for a computed tomography device, a computed tomography device and a method for cooling a computed tomography device.

BACKGROUND

In computed tomography devices the cooling concept of which is based on a central cooling fan, it is necessary to incorporate a powerful fan into the computed tomography device. This fan brings about a high flow velocity, which, if the air guidance to the central pressure duct is incorrectly designed, leads to major pressure drops and noisy flow.

SUMMARY

At least one embodiment of the invention enables improved air cooling of a computed tomography device. The claims address further advantageous aspects of the invention.

At least one embodiment of the invention relates to a cooling system for a computed tomography device, the cooling system comprising:
a fan for generating an air stream,
a fan housing for attaching the fan, wherein a first flow duct for guiding the air stream is formed in the fan housing, wherein the first flow duct widens out in a direction of flow of the air stream,
an annular frame for accommodating a rotational bearing, wherein a rotating frame of the computed tomography device is connectable to the annular frame via the rotational bearing in such a way that the rotating frame is mounted rotatably relative to the annular frame about an axis of rotation, wherein an annular second flow duct for guiding the air stream is formed in the annular frame,
wherein the fan is attached to the annular frame via the fan housing, in particular is attached immovably relative to the annular frame, in such a way that the fan is arranged outside the annular frame and the air stream is guided via the first flow duct from the fan, in particular from a pressure side of the fan, to the annular second flow duct.

At least one embodiment of the invention further relates to a computed tomography device, comprising a cooling system according to one of the disclosed aspects or embodiments.

At least one embodiment of the invention further relates to a method for cooling a computed tomography device, the method comprising
generating an air stream via a fan,
wherein the fan is attached to an annular frame of the computed tomography device via a fan housing in such a way that the fan is arranged outside the annular frame, wherein a first flow duct for guiding the air stream is formed in the fan housing, wherein the first flow duct widens out in a direction of flow of the air stream,
wherein a rotating frame of the computed tomography device is connected to the annular frame via a rotational bearing in such a way that the rotating frame is mounted rotatably relative to the annular frame about an axis of rotation, wherein a radiation source and a radiation detector are arranged on the rotating frame, in particular are arranged on the rotating frame opposite one another in relation to the axis of rotation,
wherein an annular second flow duct for guiding the air stream is formed in the annular frame; and
guiding the air stream via the first flow duct from the fan, in particular from a pressure side of the fan, to the annular second flow duct.

At least one embodiment of the invention further relates to a cooling system for a computed tomography device, comprising:
a fan to generate an air stream;
a fan housing to attach the fan, a first flow duct to guide the air stream being formed in the fan housing, wherein the first flow duct relatively widens out in a direction of flow of the air stream; and
an annular frame to accommodate a rotational bearing, a rotating frame of the computed tomography device being connectable to the annular frame via the rotational bearing, the rotating frame being mounted rotatably relative to the annular frame about an axis of rotation,
wherein an annular second flow duct to guide the air stream is formed in the annular frame, and
wherein the fan is attached to the annular frame via the fan housing, the fan being arranged outside the annular frame and the air stream is guided via the first flow duct from the fan to the annular second flow duct.

At least one embodiment of the invention further relates to a method for cooling a computed tomography device, comprising:
generating an air stream via a fan, the fan being attached to an annular frame of the computed tomography device via a fan housing such that the fan is arranged outside the annular frame, a first flow duct to guide the air stream being formed in the fan housing, the first flow duct relatively widening out in a direction of flow of the air stream,
wherein a rotating frame of the computed tomography device is connected to the annular frame via the rotational bearing such that the rotating frame is mounted rotatably relative to the annular frame about an axis of rotation, a radiation source and a radiation detector being arranged on the rotating frame,
wherein an annular second flow duct to guide the air stream is formed in the annular frame; and
guiding the air stream, via the first flow duct, from the fan to the annular second flow duct.

BRIEF DESCRIPTION OF THE DRAWINGS

The invention is explained below with reference to exemplary embodiments and to the appended figures. The depictions in the figures are schematic, highly simplified and not necessarily true to scale.

In the figures.

DETAILED DESCRIPTION OF THE EXAMPLE EMBODIMENTS

Figure 1:
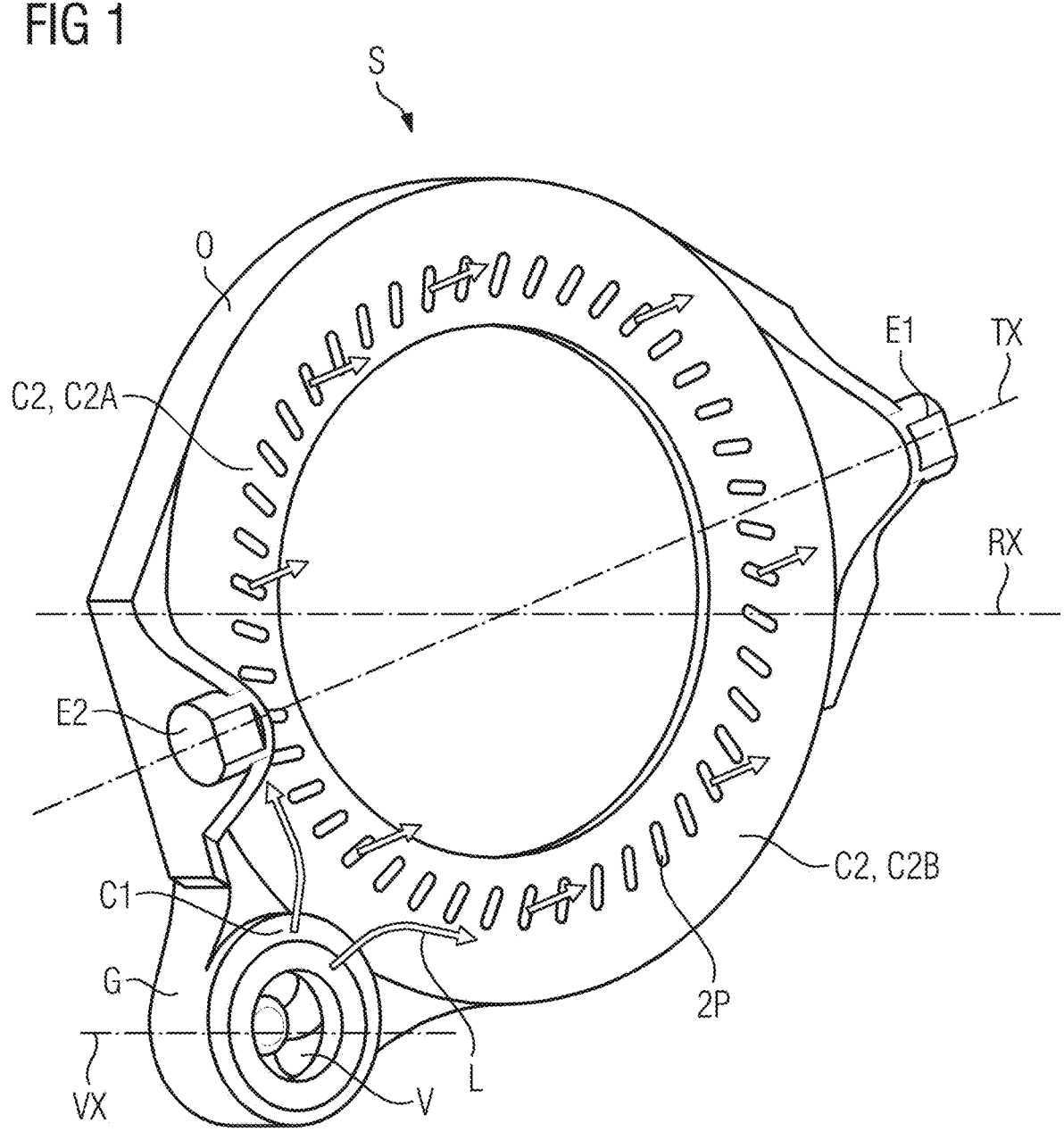
FIG. 1 shows a cooling system for a computed tomography device.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Most of the aforementioned components, in particular the identification unit, can be implemented in full or in part in the form of software modules in a processor of a suitable control device or of a processing system. An implementation largely in software has the advantage that even control devices and/or processing systems already in use can be easily upgraded by a software update in order to work in the manner according to at least one embodiment of the invention.

At least one embodiment of the invention relates to a cooling system for a computed tomography device, the cooling system comprising:

a fan for generating an air stream, a fan housing for attaching the fan, wherein a first flow duct for guiding the air stream is formed in the fan housing, wherein the first flow duct widens out in a direction of flow of the air stream, an annular frame for accommodating a rotational bearing, wherein a rotating frame of the computed tomography device is connectable to the annular frame via the rotational bearing in such a way that the rotating frame is mounted rotatably relative to the annular frame about an axis of rotation, wherein an annular second flow duct for guiding the air stream is formed in the annular frame, wherein the fan is attached to the annular frame via the fan housing, in particular is attached immovably relative to the annular frame, in such a way that the fan is arranged outside the annular frame and the air stream is guided via the first flow duct from the fan, in particular from a pressure side of the fan, to the annular second flow duct.

One embodiment provides that the first flow duct widens out in a fan-like manner in the direction of flow of the air stream and/or that the first flow duct and the annular second flow duct are arranged in a coplanar manner.

One embodiment provides that two flow paths of the air stream are formed in the annular second flow duct with opposing directions of rotation in relation to the axis of rotation. In particular, on transition from the first flow duct into the annular second flow duct, the air stream is divided between the two flow paths. In this way, the air stream may reach every region of the annular second flow duct via one of the two flow paths, of which each is significantly shorter than the length of the annular second flow duct, which substantially corresponds to the circumference of the annular frame.

The fan may in particular be a radial fan, for example a forward curved radial fan or a backward curved radial fan. For example, an axis of rotation of the radial fan, in particular an axis of rotation of a radial impeller of the radial fan, may be parallel to the axis of rotation.

The cooling system may additionally have a heat exchanger, wherein the heat exchanger is attached to the fan and/or to the fan housing and/or wherein the heat exchanger is connected to the fan, in particular to a suction side of the fan, in such a way that the fan sucks in air through the heat exchanger. The heat exchanger may for example be a water-air heat exchanger. The cooling fluid for the heat exchanger may in particular be water.

At least one embodiment of the invention further relates to a computed tomography device, comprising a cooling system according to one of the disclosed aspects or embodiments.

One embodiment provides that the computed tomography device has a radiation source, a radiation detector, a supporting frame, the rotating frame and the rotational bearing. One embodiment provides that the radiation source and the radiation detector are arranged on the rotating frame, in particular are arranged on the rotating frame opposite one another in relation to the axis of rotation. The computed tomography device may moreover inter alia have a high voltage generation unit, a radiation emitter cooler for the radiation source, a data transfer unit, an energy transfer unit and a control unit.

One embodiment provides that the rotating frame is connected to the annular frame via the rotational bearing in such a way that the rotating frame is mounted rotatably about the axis of rotation relative to the annular frame.

One embodiment provides that the computed tomography device further has a tilting frame and a tilting bearing, wherein the tilting frame is connected to the supporting frame via the tilting bearing in such a way that the tilting frame is mounted tiltably about a tilt axis relative to the supporting frame. In particular, the tilting frame may have the rotating frame, the rotational bearing, the annular frame, the fan and the fan housing.

According to one embodiment, the computed tomography device has a cooling fluid feed device, for conveying a cooling fluid for the heat exchanger from the supporting frame to the tilting frame and/or from the tilting frame to the supporting frame in the region of the tilting frame, in particular in the region of the tilt axis and/or substantially parallel to the tilt axis. In particular, the tilting frame may have the heat exchanger.

Another embodiment provides that the computed tomography device does not have a tilting frame mounted tiltably about a tilt axis relative to a supporting frame via a tilting bearing. In particular, the annular frame may be attached substantially immovably to the supporting frame.

The computed tomography device may for example have a cooling fluid feed device for conveying a cooling fluid for the heat exchanger from the supporting frame to the heat exchanger and/or from the heat exchanger to the supporting frame.

One embodiment provides that the annular frame has outlet openings for outlet of the air stream from the annular second flow duct and/or that in a component to be cooled, which is arranged on the rotating frame, a cooling duct is formed for cooling the component to be cooled. The cooling duct for cooling the component to be cooled may for example take the form of an aperture passing through the component. In particular, the component to be cooled may have a heat sink, which projects into the cooling duct in such a way that heat from the component to be cooled is transferred via the heat sink to the air stream flowing through the cooling duct.

One embodiment provides that the rotating frame has at least one opening, in particular in the form of a passage opening, on a side facing the outlet openings of the annular frame and the component to be cooled has at least one inlet opening on a side facing the at least one opening of the rotating frame, such that the air stream is guided from the outlet openings of the annular frame through the at least one opening of the rotating frame and the at least one inlet opening of the component to be cooled into the cooling duct.

In particular, it may be provided that a seal is provided between the annular frame and the rotating frame in such a way that escape of the air stream in a direction substantially perpendicular to the axis of rotation out of a gap formed between the rotating frame and the annular frame is prevented and/or that the air stream is guided from the outlet openings of the annular frame to the at least one opening of the rotating frame, in particular substantially parallel to the axis of rotation. The seal may be a brush seal, for example.

Alternatively and/or in addition to the seal, provision may be made for the gap formed between the rotating frame and the annular frame to be as narrow as possible and/or for a flow area for escape of the air stream out of the gap in a direction substantially perpendicular to the axis of rotation is relatively small, in particular significantly smaller than a resultant flow area for flow through the at least one opening in the rotating frame and the cooling duct.

One embodiment provides that the computed tomography device additionally has an enclosure, wherein the rotating frame is surrounded by the enclosure. One embodiment provides that an annular interspace is formed between the rotating frame and the enclosure and/or that the component to be cooled has at least one outlet opening for outlet of the air stream out of the cooling duct into the annular interspace.

One embodiment provides that the enclosure is substantially airtight, in particular airtight. One embodiment provides that a tunnel-shaped opening of the computed tomography device is formed in the enclosure.

The component to be cooled may for example be a radiation emitter cooler for the radiation source. The radiation emitter cooler may for example have a water circuit, for transporting heat from the radiation source to the cooling duct. The air stream enters the component to be cooled at the at least one inlet opening, cools the component to be cooled by heat transfer from the component to be cooled to the air stream and exits, heated, from the component to be cooled at the at least one outlet opening.

Further examples of the component to be cooled are the radiation detector, the high voltage generation unit, the data transfer unit, the energy transfer unit and the control unit. In particular, a plurality of components to be cooled may be arranged on the rotating frame and cooled via the air stream. In particular, the rotating frame may have in each case at least one correspondingly arranged opening for each component to be cooled.

One embodiment provides that the annular interspace is connected to the suction side of the fan via the heat exchanger in such a way that the air stream is guided from the annular interspace through the heat exchanger to the fan, in particular to the suction side of the fan.

Another embodiment provides that no heat exchanger is arranged on the fan and/or that the fan sucks in air from a surrounding environment of the computed tomography device, in particular from a surrounding environment outside the enclosure. For example, at least one air intake opening, through which the fan can suck in air from the surrounding environment of the computed tomography device, may be formed in the enclosure. In addition, at least one air outlet opening for outlet of the air stream into the surrounding environment of the computed tomography device may be formed in the enclosure. In particular, provision may be made for the air intake opening to be arranged lower than a lower edge of the tunnel-shaped opening and/or for the air outlet opening to be arranged higher than an upper edge of the tunnel-shaped opening.

At least one embodiment of the invention further relates to a method for cooling a computed tomography device, the method comprising generating an air stream via a fan,
wherein the fan is attached to an annular frame of the computed tomography device via a fan housing in such a way that the fan is arranged outside the annular frame,
wherein a first flow duct for guiding the air stream is formed in the fan housing, wherein the first flow duct widens out in a direction of flow of the air stream,
wherein a rotating frame of the computed tomography device is connected to the annular frame via a rotational bearing in such a way that the rotating frame is mounted rotatably relative to the annular frame about an axis of rotation, wherein a radiation source and a radiation detector are arranged on the rotating frame, in particular are arranged on the rotating frame opposite one another in relation to the axis of rotation,
wherein an annular second flow duct for guiding the air stream is formed in the annular frame; and
guiding the air stream via the first flow duct from the fan, in particular from a pressure side of the fan, to the annular second flow duct.

In particular, air may be sucked in through the heat exchanger via the fan.

One embodiment provides a method further comprising guiding the air stream from the annular second flow duct through outlet openings of the annular frame, at least one opening comprised by the rotating frame on a side facing the outlet openings of the annular frame and at least one inlet opening comprised by a component to be cooled on a side facing the at least one opening of the rotating frame into a cooling duct, which is formed in the component to be cooled to cool the component to be cooled, wherein the component to be cooled is arranged on the rotating frame. In particular, the component to be cooled may be cooled by the air stream guided in the cooling duct.

One embodiment provides a method further comprising guiding the air stream from the cooling duct through at least one outlet opening of the component to be cooled into an annular interspace formed between the rotating frame and an enclosure, wherein the rotating frame is surrounded by the enclosure.

One embodiment provides a method further comprising guiding the air stream from the annular interspace through a heat exchanger to the fan, in particular to a suction side of the fan.

In particular, a tilting frame of the computed tomography device may have the rotating frame, the rotational bearing, the annular frame, the fan, the fan housing and the heat exchanger. One embodiment provides that the tilting frame is connected to a supporting frame of the computed tomography device via a tilting bearing in such a way that the tilting frame is mounted tiltably relative to the supporting frame about a tilt axis, and/or that a cooling fluid for the heat exchanger is conveyed via a cooling fluid feed device, in the region of the tilting bearing, in particular in the region of the tilt axis and/or substantially parallel to the tilt axis, from the supporting frame to the tilting frame and/or from the tilting frame to the supporting frame.

At least one embodiment of the invention in particular enables air guidance requiring fewer components than conventional air guidance via an air duct connecting a fan arranged outside the tilting frame, and integrated into the supporting frame, with the tilting frame. This enables cost and space requirements to be reduced. Because the flow area is enlarged relatively significantly directly after outlet from the fan, only slight pressure drops occur. A smaller fan may thus be used or a greater pressure drop at the heat exchanger accepted.

For the purposes of the invention, features which are described in relation to different embodiments of the invention and/or different categories of claim (method, use, device, system, arrangement etc.) may be combined to yield further embodiments of the invention. For example, a claim relating to a device may also be further developed with features which are described or claimed in connection with a method and vice versa. Functional features of a method may in this case be embodied by appropriately configured physical components. In addition to the embodiments of the invention explicitly described in this application, many and varied further embodiments of the invention are conceivable, at which a person skilled in the art may arrive without going beyond the scope of the invention specified by the claims.

FIG. 1 shows a cooling system S for a computed tomography device 1, the cooling system S having the fan V for generating an air stream L, the fan housing G for attaching the fan V and the annular frame O for accommodating a rotational bearing. A first flow duct C1 for guiding the air stream L is formed in the fan housing G, wherein the first flow duct C1 widens out in a fan-like manner in a direction of flow of the air stream L.

The annular frame O is configured to accommodate a rotational bearing, wherein a rotating frame DR of the computed tomography device 1 is connectable to the annular frame O via the rotational bearing in such a way that the rotating frame DR is mounted rotatably relative to the annular frame O about an axis of rotation RX, wherein an annular second flow duct C2 for guiding the air stream L is formed in the annular frame O. The annular frame O has a first shaft piece E1 and a second shaft piece E2 for accommodation in a tilting bearing or for immovable attachment to the supporting frame F.

The fan V is a radial fan, wherein an axis of rotation VX of the radial fan is parallel to the axis of rotation RX. The fan V is arranged in an aperture of the fan housing G and attached to the annular frame O via the fan housing G in such a way that the fan V is arranged outside the annular frame O and the air stream L is guided via the first flow duct from the pressure side of the fan V to the annular second flow duct C2. The first flow duct C1 and the annular second flow duct C2 are arranged in a coplanar manner in a plane perpendicular to the axis of rotation RX.

Two flow paths C2A, C2B of the air stream L are formed in the annular second flow duct C2 with opposing directions of rotation in relation to the axis of rotation RX, wherein the air stream L is divided between the two flow paths C2A, C2B on transition from the first flow duct C1 to the annular second flow duct C2. The annular frame O has outlet openings 2P for outlet of the air stream L from the annular second flow duct C2.

Figure 2:
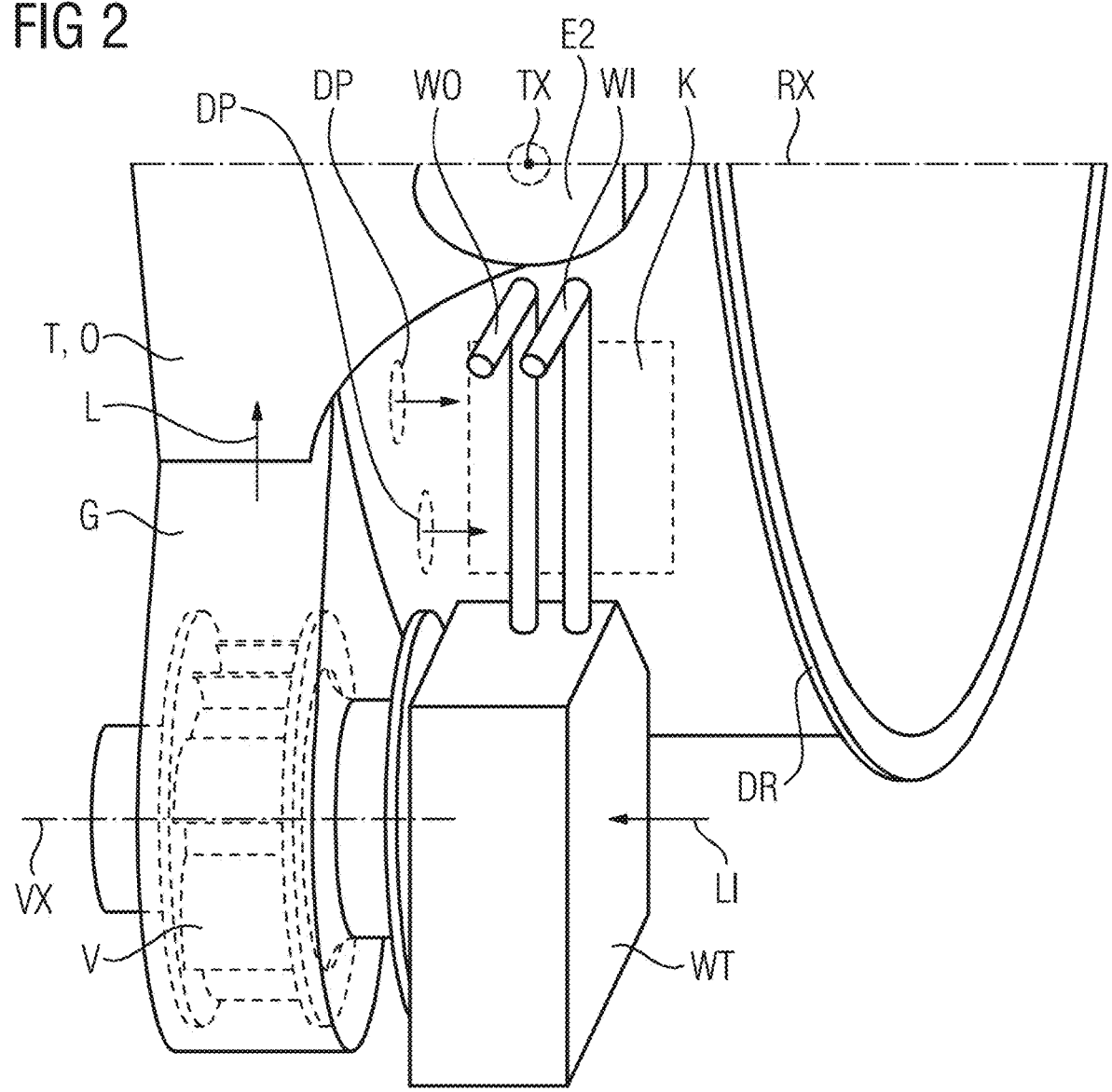
FIG. 2 shows a cooling system with a heat exchanger.

FIG. 2 shows a cooling system S having a heat exchanger WT, wherein the heat exchanger WT is attached to the fan V, wherein the heat exchanger WT is connected to the fan V in such a way that the fan V sucks in air LI through the heat exchanger WT. The tilting frame T has the heat exchanger WT. Via the first line WI of the cooling fluid feed device, a cooling fluid for the heat exchanger WT is conveyed, in the region of the tilting bearing, from the supporting frame F to the tilting frame T and into the heat exchanger WT. Via the second line WO of the cooling fluid feed device, the cooling fluid for the heat exchanger WT is conveyed out of the heat exchanger WT and from the tilting frame T to the supporting frame F. The cooling fluid feed device may for example have further components which are configured to cool the cooling fluid and/or are arranged on the supporting frame F fixedly relative to the supporting frame. The first line WI and/or the second line WO may each have at least one flexible portion and/or at least one rotary feedthrough unit, to enable the tilting motion of the tilting frame T to be followed.

Figure 3:
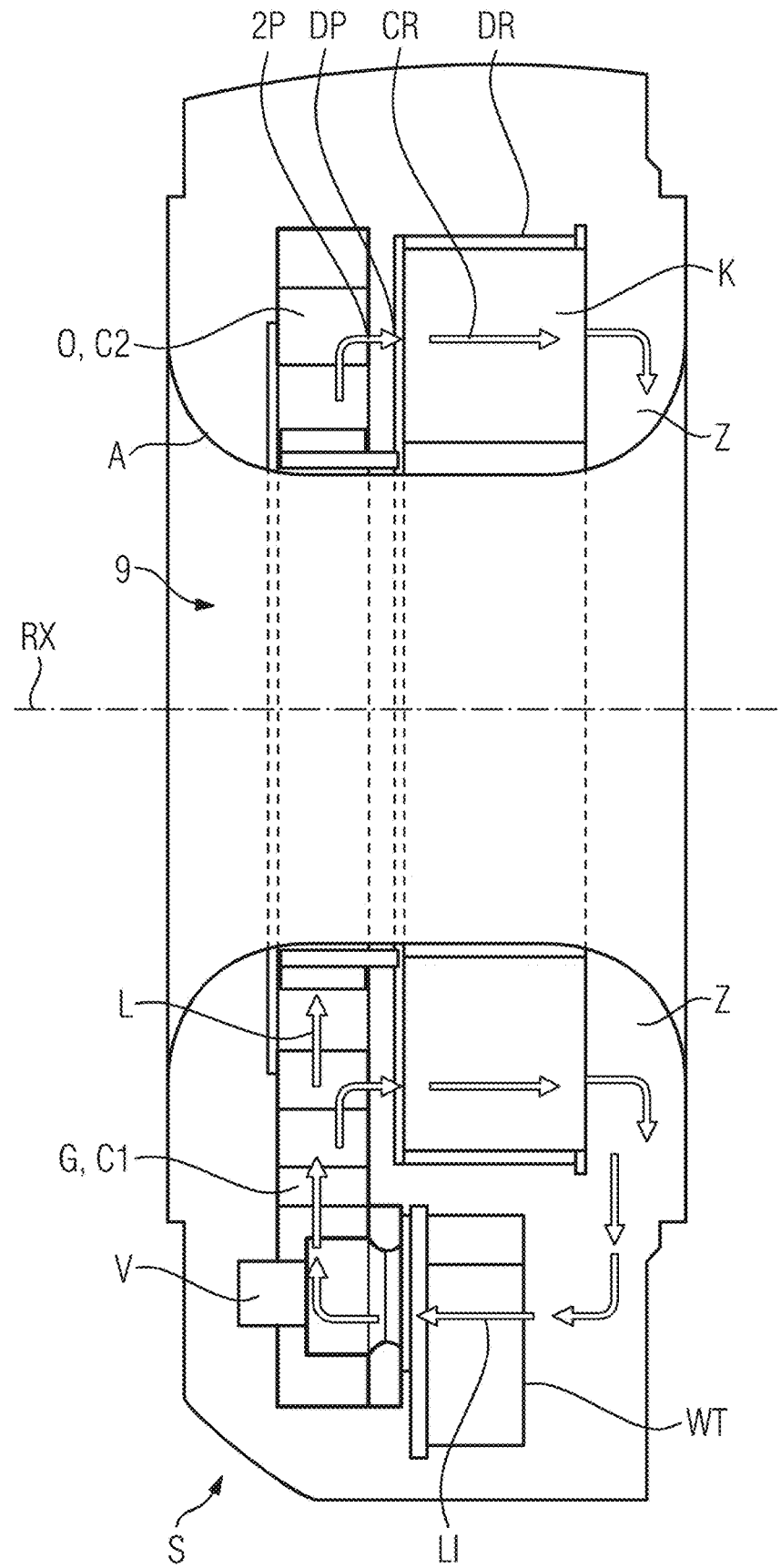
FIG. 3 shows a cooling system connected with a rotating frame.

FIG. 3 shows a cooling system connected with a rotating frame. In the component K to be cooled, which is arranged on the rotating frame DR, a cooling duct CR is formed to cool the component K, the rotating frame DR having at least one opening DP on a side facing the outlet openings 2P of the annular frame O and the component K to be cooled having at least one inlet opening on a side facing the at least one opening DP of the rotating frame DR, such that the air stream L is guided from the outlet openings 2P of the annular frame O through the at least one opening DP of the rotating frame DR and the at least one inlet opening of the component K to be cooled into the cooling duct CR. The component K to be cooled has at least one outlet opening for outlet of the air stream L from the cooling duct CR into the annular interspace Z.

The tunnel-shaped opening 9 is formed in the enclosure A. The rotating frame DR is surrounded by the enclosure A, wherein an annular interspace Z is formed between the rotating frame DR and the enclosure A, in which the air stream L may be guided.

The annular interspace Z is connected via the heat exchanger WT to the suction side of the fan V in such a way that the air stream L is guided from the annular interspace Z through the heat exchanger WT to the fan V. In this way, a closed circuit may be produced for the air stream L.

Figure 4:
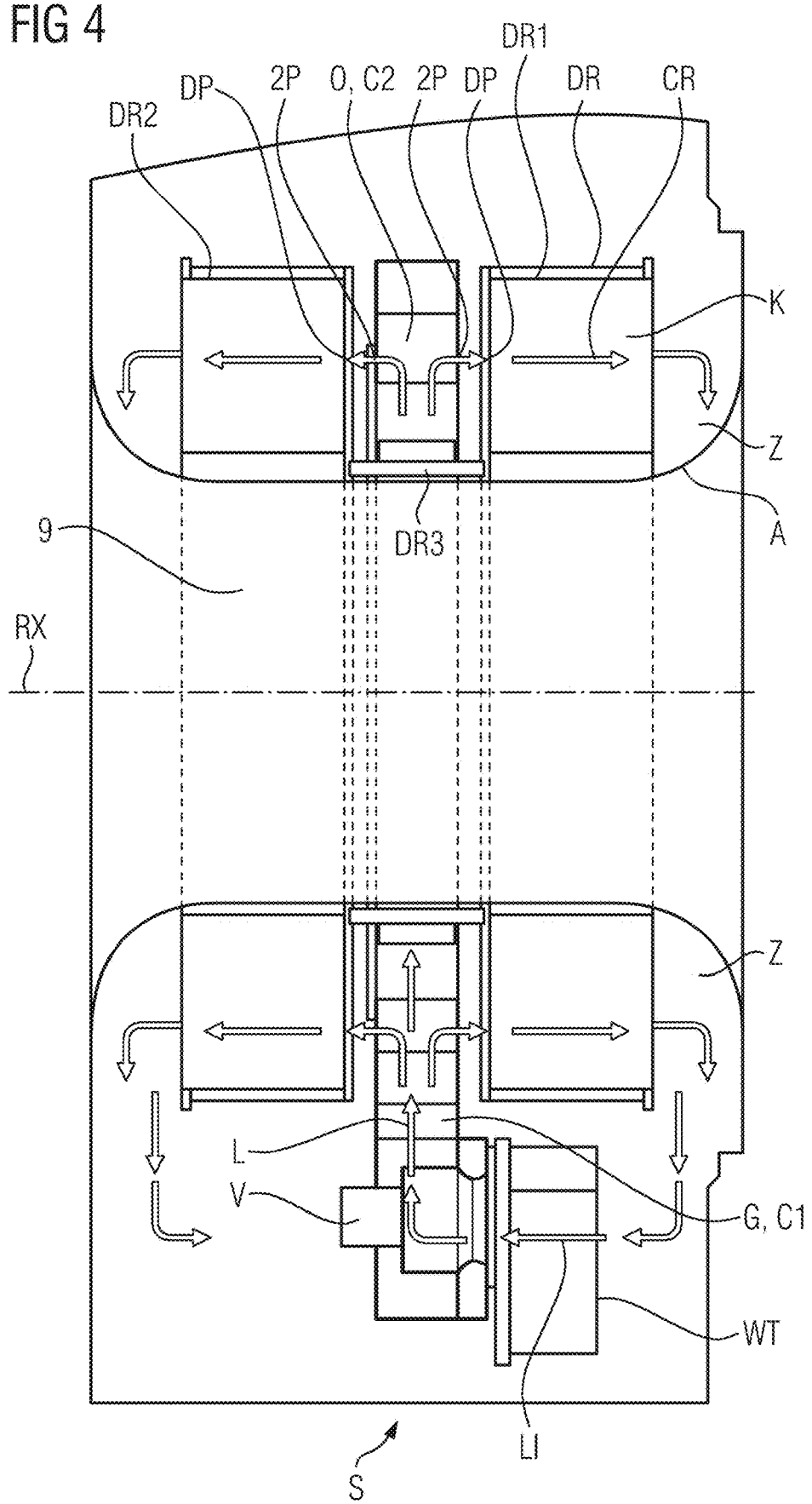
FIG. 4 shows a cooling system connected with a rotating frame, the annular frame being arranged between two portions of the rotating frame.

FIG. 4 shows a cooling system S connected with a rotating frame DR, the annular frame O being arranged between two portions of the rotating frame DR. The rotating frame DR has a first portion DR1, a second portion DR2 and a third portion DR3.

A plurality of components, for example a first radiation source, a second radiation source, a first detector interacting with the first radiation source and a second detector interacting with the second radiation source are arranged on the first portion DR1 of the rotating frame DR. A plurality of further components, for example a data transfer unit, an energy transfer unit, a control unit and a high voltage generation unit, are arranged on the second portion DR2 of the rotating frame DR. The third portion DR3 of the rotating frame DR is connected to the annular frame O via the rotational bearing.

The annular frame O has respective outlet openings 2P both on a side facing the portion DR1 and on a side facing the portion DR2 for outlet of the air stream L out of the annular second flow duct C2. The first portion DR1 of the rotating frame DR and the second portion DR2 of the rotating frame DR each have at least one opening for the air stream L on a side facing the corresponding outlet openings 2P of the annular frame O. Thus, both components arranged on the portion DR1 of the rotating frame DR and components arranged on the portion DR2 of the rotating frame DR may be cooled via the air stream L.

Figure 5:
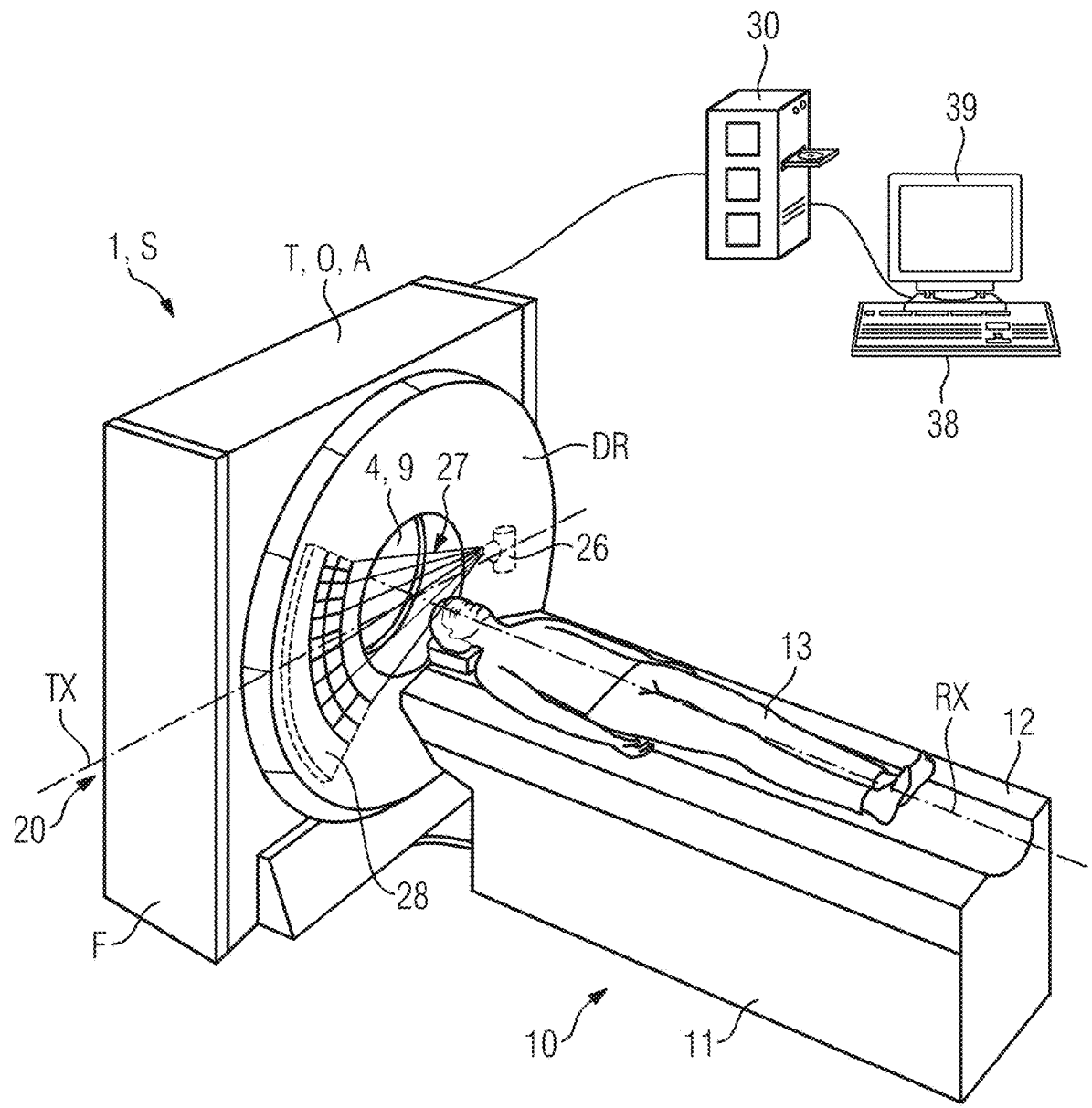
FIG. 5 shows a computed tomography device with a cooling system.

FIG. 5 shows a computed tomography device 1 having the cooling system S, a radiation source 26, a radiation detector 28, an enclosure A, a supporting frame F, a tilting frame T, a tilting bearing, the rotating frame DR and the rotational bearing. The supporting frame F, the tilting frame T, the tilting bearing, the rotating frame DR and the rotational bearing are surrounded by the enclosure A and thus located in a cavity defined by the enclosure A.

The radiation source 26 and the radiation detector 28 are arranged on the rotating frame DR opposite one another in relation to the axis of rotation RX, wherein the rotating frame DR is connected to the annular frame O via the rotational bearing in such a way that the rotating frame DR is mounted rotatably relative to the annular frame O about the axis of rotation RX. The tilting frame T is connected to the supporting frame F via the tilting bearing in such a way that the tilting frame T is mounted tiltably relative to the supporting frame F about a tilt axis TX. The tilt axis TX is perpendicular to the axis of rotation RX. The tilting frame T has the rotating frame DR, the rotational bearing, the annular frame O, the fan V and the fan housing G.

The patient 13 may be introduced into the tunnel-shaped opening 9. The acquisition region 4 is located in the tunnel-shaped opening 9. A region of the patient 13 to be imaged may be positioned in the acquisition region 4 in such a way that the radiation 27 from the radiation source 26 may reach the region to be imaged and, after interaction with the region to be imaged, may reach the radiation detector 28.

The patient positioning apparatus 10 includes the positioning base 11 and the positioning bed 12 for positioning the patient 13. The positioning bed 12 is arranged on the positioning base 11 so as to be movable relative to the positioning base 11 in such a way that the positioning bed 12 may be introduced into the acquisition region 4 in a longitudinal direction of the positioning bed 12.

The radiation source 26 is arranged on the rotating frame DR and configured to emit radiation 27, e.g. X-radiation, with radiation quanta 27. The radiation detector 28 is arranged on the rotating frame DR and configured to detect the radiation quanta 27. The radiation quanta 27 may travel from the radiation source 26 to the region of the patient 13 to be imaged and impinge on the radiation detector 28 after interaction with the region to be imaged. The computed tomography device 1 further has a control device 30, an input device 38 and an output device 39.

Figure 6:
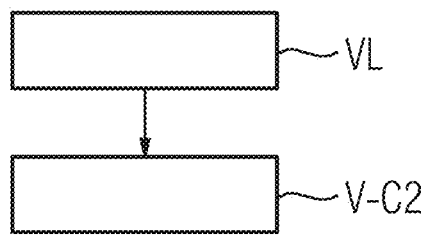
FIG. 6 shows a flowchart for a method for cooling a computed tomography device.

FIG. 6 shows a flowchart for a method for cooling a computed tomography device 1, comprising
generating VL an air stream L via a fan V,
wherein the fan V is attached to an annular frame O of the computed tomography device 1 via a fan housing G in such a way that the fan V is arranged outside the annular frame O,
wherein a first flow duct C1 for guiding the air stream L is formed in the fan housing G, wherein the first flow duct C1 widens out in a direction of flow of the air stream L,
wherein a rotating frame DR of the computed tomography device 1 is connected to the annular frame O via a rotational bearing in such a way that the rotating frame DR is mounted rotatably relative to the annular frame O about an axis of rotation RX, wherein a radiation source 26 and a radiation detector 28 are arranged on the rotating frame DR,
wherein an annular second flow duct C2 for guiding the air stream L is formed in the annular frame O,
guiding V-C2 the air stream L via the first flow duct C1 from the fan V to the annular second flow duct C2.

Figure 7:
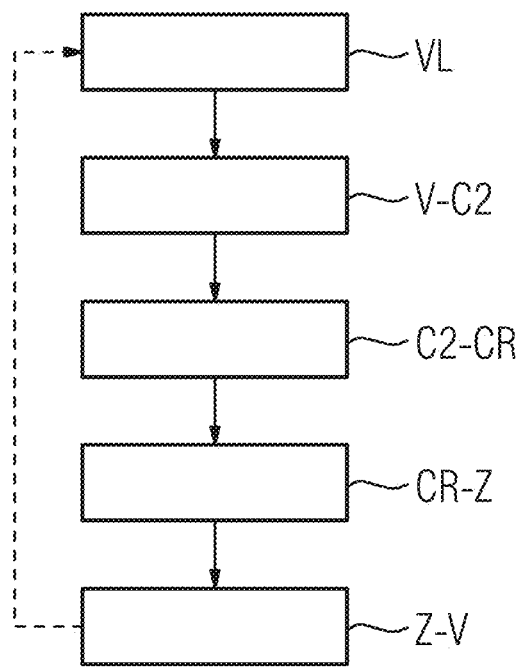
FIG. 7 shows a flowchart for a method for cooling a computed tomography device with a closed air circuit.

FIG. 7 shows a flowchart for a method for cooling a computed tomography device with a closed air circuit, further comprising
guiding C2-CR the air stream L from the annular second flow duct C2 through outlet openings 2P of the annular frame O and at least one opening comprised by the rotating frame DR on a side facing the outlet openings 2P of the annular frame O and at least one inlet opening comprised by a component K to be cooled on a side facing the at least one opening of the rotating frame DR into a cooling duct CR, which is formed in a component K to be cooled to cool the component K to be cooled, wherein the component K to be cooled is arranged on the rotating frame DR, guiding CR-Z the air stream L from the cooling duct CR of the rotating frame DR through at least one outlet opening of the component K to be cooled into an annular interspace Z formed between the rotating frame DR and an enclosure A, wherein the rotating frame DR is surrounded by the enclosure A, guiding Z-V the air stream L from the annular interspace Z through a heat exchanger WT to the fan V.

The air LI sucked in by the fan V through the heat exchanger WT is cooled via the heat exchanger WT and/or used to generate VL the air stream L via the fan V. The dashed arrow shows a closed circuit for the air stream L.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A cooling system for a computed tomography device, the cooling system comprising:
    a fan to generate an air stream;
    a fan housing to attach the fan, the fan housing having a first flow duct to guide the air stream, wherein the first flow duct widens out in a direction of flow of the air stream;
    an annular frame to accommodate a rotational bearing; and
    a heat exchanger attached to at least one of the fan or the fan housing, the heat exchanger being connected such that the fan is configured to draw in air through the heat exchanger, and the heat exchanger being configured to cool the air drawn in through the heat exchanger by the fan; wherein
    a rotating frame of the computed tomography device is connectable to the annular frame via the rotational bearing such that the rotating frame is configured to rotate relative to the annular frame about an axis of rotation and such that the annular frame is between a first portion of the rotating frame and a second portion of the rotating frame,
    the annular frame has an annular second flow duct to guide the air stream,
    the fan is attached to the annular frame via the fan housing, the fan being arranged outside the annular frame,
    the first flow duct is configured to guide the air stream from the fan to the annular second flow duct, and
    the cooling system is configured to guide the air stream into and out of the first portion of the rotating frame and the second portion of the rotating frame in a direction parallel to the axis of rotation of the rotating frame.

2. The cooling system of claim 1, wherein at least one of
    the first flow duct widens in a fan-like manner in a direction of flow of the air stream, or
    the first flow duct and the annular second flow duct are arranged to be coplanar.

3. The cooling system of claim 2, wherein
    two flow paths of the air stream are formed in the annular second flow duct with opposing directions of rotation relative to the axis of rotation, and
    the air stream is divided between the two flow paths on transition from the first flow duct to the annular second flow duct.

4. The cooling system of claim 2, wherein the fan is a radial fan.

5. The cooling system of claim 4,
    wherein an axis of rotation of the radial fan is parallel to the axis of rotation of the rotating frame.

6. A computed tomography device, comprising:
    the cooling system of claim 2.

7. The computed tomography device of claim 6, further comprising:
    a radiation source;
    a radiation detector;
    a supporting frame;
    the rotating frame; and
    the rotational bearing, wherein
        the radiation source and the radiation detector are arranged on the rotating frame, and
        the rotating frame is connected to the annular frame via the rotational bearing such that the rotating frame is configured to rotate relative to the annular frame about the axis of rotation.

8. The cooling system of claim 1, wherein
    two flow paths of the air stream are formed in the annular second flow duct with opposing directions of rotation relative to the axis of rotation, and
    the air stream is divided between the two flow paths on transition from the first flow duct to the annular second flow duct.

9. The cooling system of claim 1, wherein the fan is a radial fan.

10. The cooling system of claim 9, wherein an axis of rotation of the radial fan is parallel to the axis of rotation of the rotating frame.

11. A computed tomography device, comprising:
the cooling system of claim 1.

12. The computed tomography device of claim 11, further comprising:
a radiation source;
a radiation detector;
a supporting frame;
the rotating frame; and
the rotational bearing, wherein
the radiation source and the radiation detector are arranged on the rotating frame, and
the rotating frame is connected to the annular frame via the rotational bearing such that the rotating frame is configured to rotate relative to the annular frame about the axis of rotation.

13. The computed tomography device of claim 12, further comprising:
a tilting frame; and
a tilting bearing, wherein
the tilting frame is connected to the supporting frame via the tilting bearing such that the tilting frame is configured to tilt relative to the supporting frame about a tilt axis, and
the tilting frame includes the rotating frame, the rotational bearing, the annular frame, the fan and the fan housing.

14. The computed tomography device of claim 13, further comprising:
a cooling fluid feed device to convey a cooling fluid for the heat exchanger at least one of (i) from the supporting frame to the tilting frame in a region of the tilting bearing or (ii) from the tilting frame to the supporting frame, wherein
the tilting frame includes the heat exchanger.

15. The computed tomography device of claim 12, wherein
the annular frame includes outlet openings for outlet of the air stream from the annular second flow duct,
a cooling duct is formed for cooling a component to be cooled that is arranged on the rotating frame, and
the rotating frame includes at least one opening on a side facing the outlet openings of the annular frame and the component to be cooled includes at least one inlet opening on a side facing the at least one opening of the rotating frame, such that the air stream is guided from the outlet openings of the annular frame through the at least one opening of the rotating frame and the at least one inlet opening of the component to be cooled into the cooling duct.

16. The computed tomography device of claim 15, further comprising:
an enclosure, wherein
the rotating frame is surrounded by the enclosure,
an annular interspace is formed between the rotating frame and the enclosure, and
the component to be cooled has at least one outlet opening for outlet of the air stream from the cooling duct into the annular interspace.

17. The computed tomography device of claim 16, wherein the annular interspace is connected to a suction side of the fan via the heat exchanger such that the air stream is guided from the annular interspace through the heat exchanger to the fan.

18. The cooling system of claim 1, further comprising:
a tilting frame; and
a tilting bearing, wherein
the tilting frame is configured to connect to a supporting frame of the computed tomography device via the tilting bearing such that the tilting frame is configured to tilt relative to the supporting frame about a tilt axis,
the tilting frame includes at least the annular frame, the fan, the fan housing and the heat exchanger; and
a cooling fluid feed device configured to convey a cooling fluid for the heat exchanger at least one of (i) from the supporting frame to the tilting frame or (ii) from the tilting frame to the supporting frame.

19. A method for cooling a computed tomography device, the method comprising:
generating an air stream via a fan, the fan being attached to an annular frame of the computed tomography device via a fan housing such that the fan is arranged outside the annular frame, the fan housing having a first flow duct to guide the air stream, the first flow duct widening out in a direction of flow of the air stream, wherein
a rotating frame of the computed tomography device is connected to the annular frame via a rotational bearing such that the rotating frame is configured to rotate relative to the annular frame about an axis of rotation and such that the annular frame is between a first portion of the rotating frame and a second portion of the rotating frame,
a radiation source and a radiation detector are arranged on the rotating frame,
the annular frame has an annular second flow duct to guide the air stream;
cooling air drawn in through a heat exchanger by the fan, the heat exchanger being attached to at least one of the fan or the fan housing;
guiding the air stream, via the first flow duct, from the fan to the annular second flow duct; and
guiding the air stream in and out of the first portion of the rotating frame and the second portion of the rotating frame in a direction parallel to the axis of rotation of the rotating frame.

20. The method of claim 19, further comprising:
guiding the air stream from the annular second flow duct through outlet openings of the annular frame, wherein
at least one opening is comprised by the rotating frame on a side facing the outlet openings of the annular frame,
at least one inlet opening is comprised by a component to be cooled on a side facing the at least one opening of the rotating frame into a cooling duct,
the cooling duct is formed in the component to be cooled to cool the component to be cooled, and
the component to be cooled is arranged on the rotating frame.

21. The method of claim 20, further comprising:
guiding the air stream from the cooling duct through at least one outlet opening of the component to be cooled into an annular interspace formed between the rotating frame and an enclosure, wherein
the rotating frame is surrounded by the enclosure.

22. The method of claim 21, further comprising:
guiding the air stream from the annular interspace to the fan through the heat exchanger.

23. The method of claim 22, wherein
a tilting frame of the computed tomography device includes the rotating frame, the rotational bearing, the annular frame, the fan, the fan housing and the heat exchanger,
the tilting frame is connected to a supporting frame of the computed tomography device via a tilting bearing such that the tilting frame is configured to tilt relative to the supporting frame about a tilt axis, and a cooling fluid for the heat exchanger is conveyed via a cooling fluid feed device at least one of (i) from the supporting frame to the tilting frame in a region of the tilting bearing or (ii) from the tilting frame to the supporting frame.

\* \* \* \* \*